United States Patent
Chi (12)

(10) Patent No.: US 6,436,702 B1
(45) Date of Patent: Aug. 20, 2002

(54) **IMMORTAL CELL LINE DERIVED FROM GROUPER *EPINEPHELUS COIOIDES* AND ITS APPLICATION THEREIN**

(75) Inventor: Shau-Chi Chi, Taipei (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/450,696

(22) Filed: Nov. 30, 1999

Related U.S. Application Data

(60) Provisional application No. 60/110,699, filed on Dec. 3, 1998.

(51) Int. Cl.$^7$ ............................... C12N 5/00; C12N 7/00
(52) U.S. Cl. .................... 435/325; 435/235.1; 435/239; 424/204.1
(58) Field of Search .............................. 435/239, 235.1, 435/325; 424/204.1, 817

(56) References Cited

U.S. PATENT DOCUMENTS

| | | |
|---|---|---|
| 5,135,864 A | 8/1992 | Montagnier et al. |
| 5,236,840 A | 8/1993 | Loh et al. |
| 5,602,022 A | 2/1997 | Van Der Marel et al. |

OTHER PUBLICATIONS

Chi et al., Journal of Fish Diseases, May 1999, vol. 22, No. 3, pp. 173–182, 1999.*
Chi et al., Virus Research, Sep., 1999, vol. 63, No. 1–2, pp. 107–114, 1999.*
S.C. Chi et al.; Mass mortalities associated with viral nervous necrosis (VNN) disease in two species of hatchery–reared grouper, *Epinephelus fuscogutatus* and *Epinepheius akaara*; Journal of Fish Diseases, 1997, pp. 185–193, vol. 20; Blackwell Science Ltd.

Shau–Chi Chi; The Investigation of Viral Disease among Cultured Groupers in Southern Taiwan; COA Fisheries Series, 1997, pp. 59–69, vol. 61.

* cited by examiner

*Primary Examiner*—Laurie Scheiner
(74) *Attorney, Agent, or Firm*—Fei-Fei Chao; Venable, Baetjer, Howard & Civiletti, LLP

(57) ABSTRACT

The present invention describes (1) an immortal cell line derived from grouper and a method for establishing the cell line; (2) methods for mass producing and purifying aquatic viruses using the immortal cell line from grouper; (3) an anti-NNV antibody and a method for producing the anti-NNV antibody; and (4) a vaccine of NNV and a method for protecting fish against NNV infection. The present immortal cell line is derived from the grouper and is susceptible to the viral families of Birnaviridae such as Infectious Pancreatic Necrosis Virus (IPNV); Herpesviridae such as Eel Herpes Virus Formosa (EHVF); Reoviridae such as Hard Clam Reovirus (HCRV); and Nodaviridae such as Nervous Necrosis Virus (NNV).

8 Claims, 10 Drawing Sheets

Figure 1A:
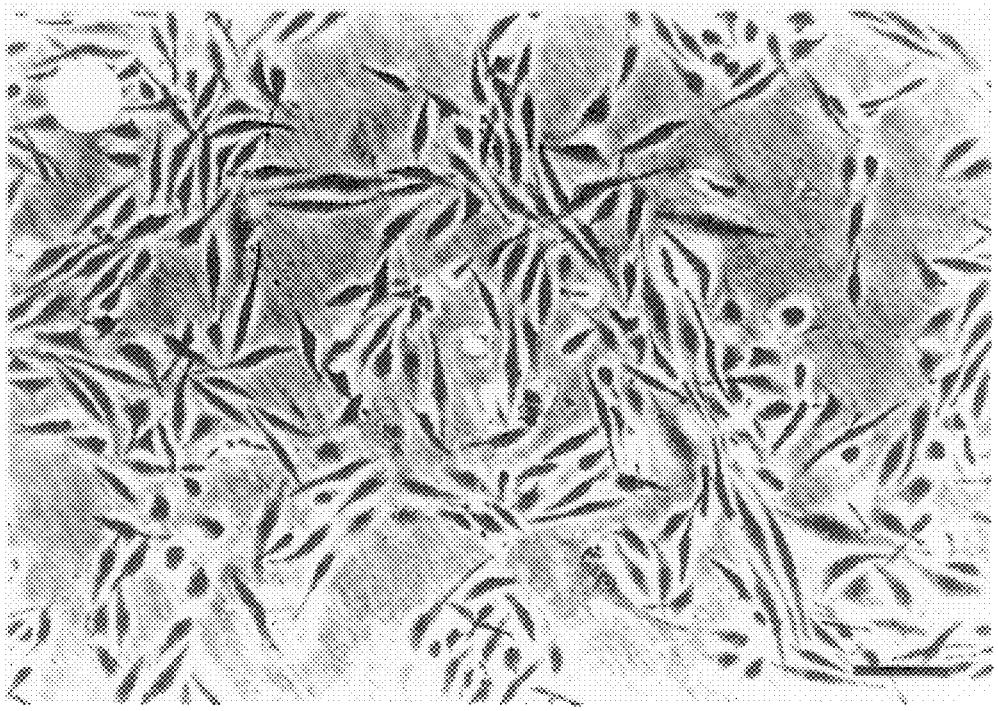

IMMORTAL CELL LINE DERIVED FROM GROUPER *EPINEPHELUS COIOIDES* AND ITS APPLICATION THEREIN

RELATED APPLICATION

This application claims the priority of U.S. Provisional Application No. 60/110,699, filed on Dec. 3, 1998, which is incorporated herein by reference.

FIELD OF THE INVENTION

The present invention relates to an immortal cell line (GF-1) derived from the fin tissue of grouper *Epinephelus coioides* and the method of establishing the GF-1 cell line. The GF-1 cell line is susceptible to a number of aquatic viruses, including, but not limited to, Infectious Pancreatic Necrosis Virus (IPNV), Eel Herpes Virus Formosa (EHVF), and Nervous Necrosis Virus (NNV). This invention also relates to the method of mass producing and purifying the aquatic viruses using an immortal cell line from grouper such as the GF-1 cell line as a host. Additionally, this invention relates to an anti-NNV antibody and the method of producing the anti-NNV antibody. Finally, this invention relates to a vaccine of NNV and the method for protecting fish against NNV infection.

BACKGROUND OF THE INVENTION

Nervous necrosis virus (NNV), a pathogen found in many varieties of hatchery-reared marine fish, has caused mass mortality of such fish at their larval or juvenile stages. NNV belongs to the family Nodaviridae. Fish nodaviruses isolated from different species (such as SJNNV, BFNNV, JFNNV, TPNNV, RGNNV, GNNV etc.) are closely related to each other owing to the high similarity of the conserved region of their coat protein genes. NNV, also named as fish encephalitis virus (FEV) and piscine neuropathy nodavirus (PNN), is an unenveloped spherical virus with particles sized between 25 and 34 nm. The virus is characterized by vacuolation of the nerve tissues. Viral Nervous Necrosis (VNN) disease has been found in many countries under various names such as viral fish encephalitis, fish encephalomyelitis, cardiac myopathy syndrome. The hosts of NNV include many species of marine fish, for example: parrotfish, sea bass, turbot, grouper, stripped jack, tiger puffer, berfin flounder, halibut, barramundi, and spotted wolffish.

According to the statistics shown in 1993, approximately 159 fish cell lines have been established which have demonstrated a capacity for growing fish viruses (Fryer and Lannan, *J. Tissue Culture Method* (1994), 10:57–94). Most of these cell lines are derived from the tissues of freshwater fish. There are only thirty-four cell lines which are originated from marine fish. Although some of the fish cell lines, which include RTG-2, CHSE-214, BF2, SBL, FHM, EPC, have been tested for the susceptibility of fish nodavirus, none of these cells lines has shown cytopathic effects (CPE) after viral inoculations.

In 1996, SSN-1 cell line, a cell line derived from striped snakehead *Channa Striatus*, has been successfully used for isolating sea bass nodavirus (Frerichs et al., *J. General Virology* (1996)77:20672071). However, SSN-1 cell line has been known to be persistently contaminated with C-type retrovirus (Frerichs et al., *J. General Virology* (1991) 72:2537–2539). Therefore, it is not suitable for the production of fish nodavirus.

Viral diseases cannot be cured by therapeutic reagents. The best ways to contain viral diseases include prevention through early detection and the development of vaccines. In either way, the understanding of the biological, biochemical, and serological characteristics of the virus is fundamentally required, which in turn relies on the industry to have the capacity of mass producing the pure form of viruses, preferably through an in vitro cell culture system. Therefore, the development of a new cell line which can be susceptible to fish nodavirus is desperately in demand in order to control the wide spread of fish viral diseases due to fish nodavirus infection.

Grouper is an important hatchery fish in Taiwan. In recent years, there have been several reports regarding the establishment of cell lines derived from grouper. For example, Chen et. al. (*Japan Scientific Society Press* (Tokyo) (1988) 218–227) have reported their establishment of several cell lines from the fin and kidney tissues of grouper *Epinephelus awoara*. Lee (Master Thesis from the Department of Zoology at the National Taiwan University, 1993) also has reported his establishment of the cell lines derived from the eye pigment cells and brain tissue of grouper *Epinephelus amblycephalus*. However, Chen et al. do not provide sufficient data in support of the claim for immortality in their cell lines and Lee expressly indicates in his thesis that his grouper cell lines are not immortal. Moreover, neither Chen et al.'s nor Lee's cell lines are susceptible to fish nodavirus.

Recently, severe mortality among groupers has repeatedly occurred which is caused primarily by nodavirus. As present, fish nodavirus has been discovered in grouper and can be isolated from moribund grouper which possess symptoms of VNN disease (Chi et al.,*J. Fish Disease* (1997) 20:185–193). Electron microscopic examination of the tissues from grouper shows that, in addition to nodavirus infection, grouper is susceptible to other viral infections (Chi, *COA Fisheries Series No.61, Reports on Fish Disease Research* (1997) 18:59–69). The fact that some viruses have host specificity makes a cell line derived from grouper more appropriate for investigating the specific viruses isolated from grouper.

In the invention to be presented below, an immortal cell line derived from the fin tissue of grouper *Epinephelus coioides* (Hamilton) will be introduced: The cell line of the present invention is susceptible to various viruses, particularly fish nodavirus such as GNNV. Using the present cell line, various aquatic viruses can be mass produced and purified. The purified viruses are useful for antibody and vaccine production to protect fish from viral infections.

SUMMARY OF THE INVENTION

A first embodiment of the present invention provides for an immortal cell line derived from grouper, preferably, an immortal cell line (GF-1) which is derived from the fin tissue of grouper *Epinephelus coioides*. GF-1 is susceptible to, and can mass produce viruses which include, but are not limited to, viruses from the families of Birnaviridae (such as infectious pancreatic necrosis virus [IPNV]), Herpesviridae (such as eel herpes virus Formosa [EHVF]), Reoviridae (such as hard clam reovirus [HCRV]), and Nodaviridae (such as grouper nervous necrosis virus [GNNV]).

The first embodiment also provides for a method of establishing an immortal cell line. The method comprises the steps of : (1) establishing a primary cell culture by placing cells released from the fin tissue of grouper *Epinephelus coioides* in a tissue culture flask to form a monolayer of cells; (2) subculturing and maintaining the monolayer of cells in a media suitable for cell subculturing; and (3) monitoring a transformation of cells which is characterized by a change in chromosome number distribution, plating efficiency, fetal bovine serum (FBS) requirement, and susceptibility to aquatic viruses, particularly fish nodavirus such as GNNV.

A second embodiment of the invention provides for a method for growing a virus using the immortal cell line derived from grouper, preferably the GF-1 cell line. The method comprises the steps of. (1) inoculating the virus into the cell line; and (2) incubating the cell line in a nutrient medium suitable for growth and replication of the virus. The viruses which are susceptible to and can be replicated in the immortal cell line include viruses from the families of Birnaviridae, Herpesviridae, Reoviridae, and Nodaviridae, and, in particular, lPNV of Birnaviridae, EHVF of Herpesviridae, HCRV of Reoviridae, and GNNV of Nodaviridae.

The second embodiment also provides for methods of mass producing the viruses using the immortal grouper cell line, purifying the viruses, and detecting the viruses in the cell line. The method for mass producing the virus comprises: (1) inoculating the virus into the grouper cell line; (2) incubating the cell line in a nutrient medium suitable for growth and replication of the virus; and (3) harvesting the virus from the cell line.

The method for purifying a virus comprises: (1) inoculating the virus into the grouper cell line; (2) incubating the cell line in a nutrient medium suitable for growth and replication of the virus until the appearance of cytopathic effects (CPE); (3) harvesting the virus from the cell line; and (4) purifying the virus using density gradient centrifugation. The preferable density gradient is a CsCl density gradient. However, other density gradients which yield a sufficient virus harvest are also within the scope of the invention.

The present method for detecting a virus in the immortal grouper cell line comprises: observing a development of cytopathic effects (CPE) in the cell line under microscope. The virus can be further confirmed by the electron microscopic method which comprises the steps of. (1) fixing the cell line in glutaraldehyde and osmium tetraoxide; (2) performing ultrathin sectioning of the fixed cells; and (3) detecting viral particles in the ultrathin section of the fixed cell line under an electron microscope.

There are four methods which contribute to the specific detection of NNV in the immortal grouper cell line after the CPE is detected in the cell line. A first method uses the polymerase chain reaction (PCR), which comprises the steps of: (1) extracting a viral RNA from the cell line; (2) amplifying the viral RNA by PCR using a reverse primer (SEQ ID NO. 1) and a forward primer (SEQ ID NO.2). A second method uses a western immunoblot, which comprises the steps of. (1) extracting the viral protein from the cell line; (2) electrophoresizing the viral protein in an SDS-polyacrylamide gel; and analyzing the polyacrylamide gel by western immunoblot using an anti-NNV serum. A third method uses an enzyme-linked immunosorbent assay (ELISA) method to detect NNV protein. A fourth method uses immunofluorescent staining by coupling fluorescein isothiocyanate (FITC) conjugated goat anti-mouse antibodies with mouse anti-NNV serum to thereby detect NNV within the cells.

A third embodiment of the invention provides for an anti-NNV antibody and a method of making the anti-NNV antibody. The anti-NNV antibody is preferably a monoclonal antibody. The anti-NNV antibody is prepared by administering an effective amount of NNV to a suitable animal, preferably a mouse or a rabbit, to stimulate an immunoresponse in the animal. The NNV used for making the anti-NNV antibody is preferably the one harvested from the grouper cell line and further purified by a CsCl density gradient centrifugation (NNV has a buoyant density of approximately 1.34 g/ml in CsCl).

A fourth embodiment of the invention provides for a vaccine to NNV and a method for protecting fish against NNV infection. The NNV vaccine comprises an immunogenically effective amount of killed NNV. The vaccine further comprises a material selected from the group consisting of adjuvants, plasticizers, pharmaceutical excipients, diluents, carriers, binders, lubricants, glidants and aesthetic compounds, and combinations thereof. The vaccine can be administered orally or by injection. Oral administration is the preferred method of vaccinating fish. For the orally administered vaccine, an enteric coating which is impervious to dissolution in the stomach of fish can be added to the vaccine. The NNV useful for making the anti-NNV antibody is preferably the one harvested from the grouper cell line and further purified by a CsCl density gradient centrifugation (NNV has a buoyant density of approximately 1.34 g/ml in CsCl). The NNV is preferably inactivated. The present method for protecting fish against NNV infection comprises: administrating an effective amount of the NNV vaccine to a fish.

BRIEF DESCRIPTION OF THE DRAWINGS

FIGS. 1A and 1B show the morphology of the GF-I cells observed under an inverted microscope. (1A) A semi-confluent monolayer where both fibroblast-like and epithelial cells co-existed, and (1B) a confluent monolayer of GF-1 cells at subculture 80 where fibroblast-like cells were the predominant cells. In the figure, an arrowhead indicates fibroblast-like cells. Similarly, an arrow indicates epitheloid cells. Bar=10 $\mu$m FIGS. 2A and 2B show the chromosome number distribution of the GF-1 cells at (2A) subculture 50, and (B) subculture 80.

FIGS. 3A and 3B shows the effect of fetal bovine serum (FBS) on the growth rate of GF-1 cells at (3A) subculture 50, and (3B) subculture 80.

FIG. 4 shows the effect of temperature on the growth rate of GF-1 cells at subculture 80.

FIGS. 5A–5H shows the cytopathic effects (CPE) of GF-1 cells at subculture 80 after infection by (5A) IPNV AB strain, (5B) IPNV SP strain, (5C) IPNV VR299 strain, (5D) IPNV EVE strain, (5E) HCRV, (5F) fish nodavirus_GNNV isolate, and (G) HEVF, as compared with (H) Uninfected GF-1 cells.

FIG. 6 shows the agarose gel electrophoresis of the product by RT-PCR amplification using a pair of primers (SEQ ID NO: 1 and SEQ ID NO:2) specific to the target region T4 of fish nodavirus SJNNV. Lane 1, PCR product from GNNV-infected GF-1 cells; lane 2, PCR product from non-infected GF-1 cells. M: pGEM marker.

FIG. 7 is an electron micrograph of GNNV-infected GF-1 cells. Inclusion bodies (indicated by arrowhead) and numerous non-enveloped viral particles are shown in the cytoplasm. I: an inclusion body filled with viral particles. M: mitochondria, N: nucleus. Arrowhead indicates the viral particle. Bar=1 $\mu$m.

DETAILED DESCRIPTION OF THE INVENTION

In accordance with a first embodiment of the present invention, there is provided an immortal cell line which is derived from grouper, preferably from the grouper *Epinephelus coioides*, and more preferably from the fin tissue of grouper *Epinephelus coioides*. A vital sample of the immortal cell line derived from the fin tissue of grouper *Epinephelus coioides*, the GF-1 cell line, was deposited at the American Type Culture Collection (ATCC), 10801 University Blvd., Manassas, Va. 20110-2209, on Oct. 20, 1999, in compliance with the provisions of the Budapest Treaty for the International Recognition of the Deposit of Microorganisms for the Purpose of Patent Procedure. The assigned deposit number for this cell line is ATCC No. PTA-859. The viability of the GF-1 cell line was tested and confirmed on Nov. 1, 1999. The strain will be made available if a patent office signatory to the Budapest Treaty certifies one's right to receive, or if a U.S. Patent is issued citing the strain, and ATCC is instructed by the United States Patent And Trademark Office or the depositor to release the strain.

This embodiment also provides for a method of establishing an immortal cell line. The experimental designs and results pertaining to the establishment of an immortal cell line are illustrated, but not limited to, in the following examples:

EXAMPLE 1

ESTABLISHMENT OF THE GF-1 CELL LINE

The GF-1 cell line was established and maintained as follows:

(1) Primary Culture

A grouper (*Epinephelus coioides*, Hamilton) weighing 1 kg was used for the establishment of the primary culture. The fish was dipped in 5% chlorex for 5 min, and then wiped with 70% alcohol. The fin was dissected from the body, and washed three times in a washing medium (containing L15 plus 400 IU/ml of penicillin, 400 µg/ml of streptomycin and 10 pg/ml of fungizone). After washing, the fin tissue was minced with scissors and then placed into 0.25% trypsin solution (0.25% trypsin and 0.2% EDTA in phosphate-buffered saline[PBS]). The tissue fragments in trypsin solution were slowly agitated with a magnetic stirrer at 4° C. At 30 min intervals, cells released from the tissue fragment were collected by centrifugation. Next, cells were re-suspended in a complete medium (containing L15 plus 20% of fetal bovine serum [FB-S], 100 IU/ml of penicillin, 100 µg/ml of streptomycin, and 2.5 µg/ml of fungizone), transferred into a 25 cm² tissue culture flask and, finally, cultured at 28° C.

(2) Subculture and Maintenance

When the confluent monolayer of cells had formed in the primary culture, cells were dislodged from the flask surface by treating with 0.1% trypsin solution (containing 0.1% of tryspin and 0.2% of EDTA in PBS). The released cells were then transferred into two new flasks containing fresh L15 medium plus 20% of FBS. Cells were subcultured at a split ratio of 1:2. For the first ten subcultures of the GF-1 cells, a conditioned medium consisting of 50% old and 50% fresh medium was used. The concentration of FBS in the maintaining L15 medium was 10% for subcultures 11–70, and decreased to 5% after subcultures 70. Also, during the first twenty passages, GF-1 cells were subcultured at a 9-day interval. For the next $21^{th}$–$70^{th}$ passages, the GF-1 cells were subcultured at a 5-day interval. After 71 passages, GF-1 cells were subcultured at a 3-day interval.

(3) Test for Mycoplasma Contamination in the GF-1 Cell line

The GF-1 cell line was propagated for three transfers in antibiotic-free L15-10% FBS and tested for the presence of bacteria, fungi, and mycoplasma. A mycoplasma stain kit (Flow Laboratories, U.S.A.) was used for mycoplasma testing.

(4) Test for the Viability of the GF-1 Cell Line

The viability of the GF-1 cell line was tested by first removing the cells from the flask. Then, the cells were separated from the medium by centrifugation, and re-suspended in a freezing medium consisting of 10% dimethyl sulfoxide (DMSO) and 90% FBS. Ampules (NUNC, Denmark) containing $5 \times 10^6$ cells/ml /ampule were held at −20° C. for one hour, followed by staying at −70° C. overnight before being transferred to liquid nitrogen (−176° C.). After one month and one year, the ampules were thawed in a 30° C. water bath. The cells were separated from the freezing medium by centrifugation. The cells were re-suspended in L15-10% FBS. The viable cells were determined by trypan blue staining. The number of cells was counted using a hemacytometer. The thawed cells were re-seeded into a 25 cm² flask for further observation.

(5). Chromosome Number Distribution

The distribution of the chromosome numbers in GF-1 cells at subculture 50 and subculture 80 were studied using semi-confluent and actively growing cells. Cells were pre-treated with 0.1 µg/ml Colcemid (Gibco, Grand Island, N.Y.) for 5 hours at 28° C. before being dislodged with 0.1% of trypsin solution. After centrifugation at 1000 g for 10 min, the cells were re-suspended in a hypotonic solution (containing 8 parts of distilled water and 1 part of PBS) for 30 min. The cells were then partially fixed by adding several drops of Carnoy fixative (containing 1 part of Glacial acetic acid and 3 parts of 100% methanol). The partially fixed cells were further centrifuged at 800 g for 10 min at 4° C. The supernatant was discarded, and the cells were fixed in fresh, cold Carnoy fixative for 20 min. The suspension of fixed cells was dropped onto a 76×26 mm slide. The slide was air-dried and the cells were stained with 0.4% Giemsa stain (Sigma, St. Louis, Mo., USA) for 30 min. The chromosome numbers were observed and counted under an Olympus Vanox microscope.

(6) Plating Efficiency

The plating efficiency of the GF-1 cells was estimated at subcultures 50 and 80. Cells were seeded into a 25 cm² flask at a density of 100 cells per flask. Following 15 days of incubation, the medium was removed and the cell colonies were fixed with 70% ethanol and stained with 0.4% Giemsa. The colonies in each flask were then counted using an Olympus IM inverted microscope. Carp fin (CF), black porgy spleen (BPS-1), tilapia ovary (TO-2) and eel kidney (EK) cell lines were plated the same way as the GF-1 cell line for comparison purpose.

(7) Effects of FBS Concentration and Temperature on the Growth of the GF-1 Cells The effects of the concentration of FBS on GF-1 cell growth were determined at subcultures 50 and 80. Two replicates were prepared for each FBS concentration. At selected intervals, two flasks were withdrawn from each concentration of FBS, and the mean number of cells was counted.

To determine the effects of temperature on the growth of GF-1 cells at subculture 80, replicated cell cultures in 25 cm² flasks containing L15-10% FBS were incubated at 18° C., 28° C. and 35° C. The mean number of the GF-1 cells from two replicated flasks at each temperature was counted at selected intervals.

Results

Primary Culture and Subculture of the GF-1 Cells

Figure 1B:
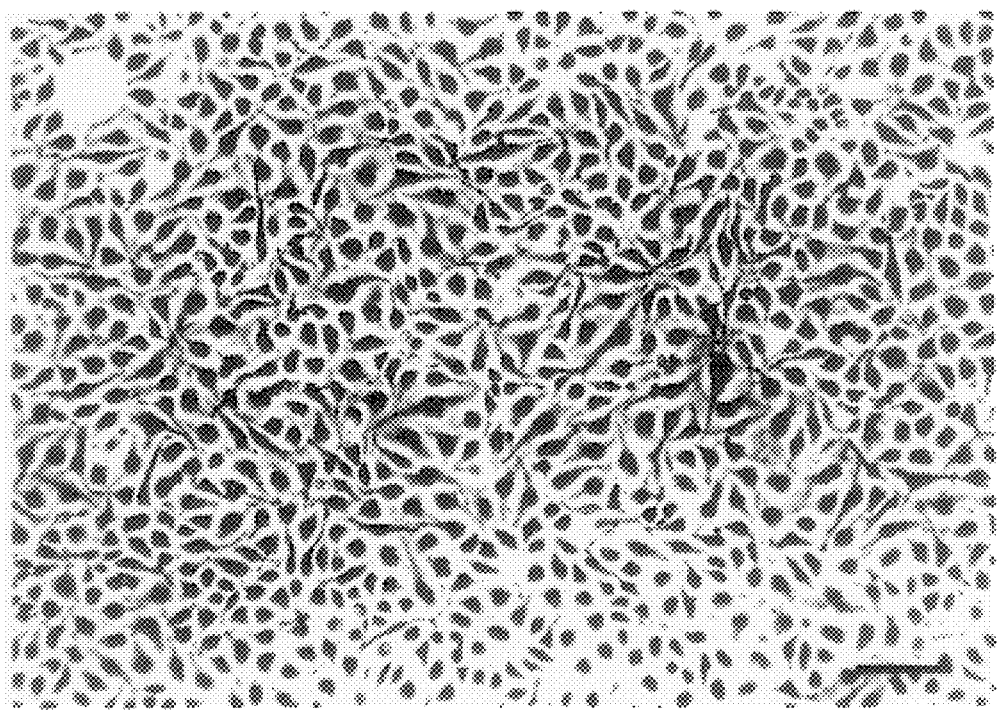

A monolayer of cells was formed in the primary culture approximately two weeks after the implantation. Fibroblastlike cells and epitheloid cells co-exist in the cell population (FIG. 1). The GF-1 cells have been successfully subcultured for more than 160 times since 1995, subsequently becoming a continuous cell line.

The GF-1 cells were subcultured at 9-day intervals in L15-20% of FBS during the first twenty subcultures, at 5-day intervals in L15-10% of FBS during the $21^{st}$–$70^{th}$ subcultures, and at 3-day intervals in L15-5% of FBS since subculture 71. Contact inhibition of the GF-1 cells was found in cultures before subculture 50, and gradually decreased between subculture 51 and 80.

The viability of the GF-1 cells at subculture 80 after one year and one month was 73%. The re-seeded cells grew readily when incubated at 28° C. in L15-5% of FBS.

Chromosome Number

Figure 2A:
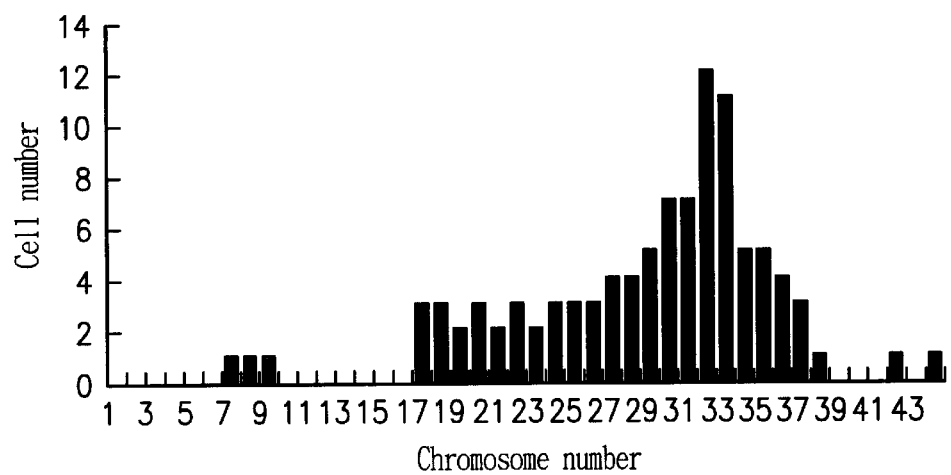
Figure 2B:
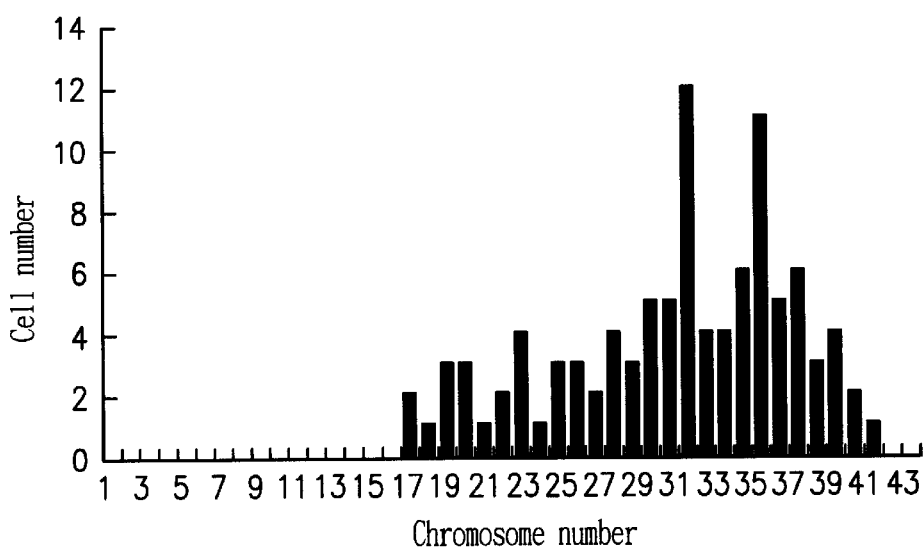

The chromosome number of the GF-1 cells at subculture 50 was distributed between 7 and 44 with the mode set at 32 (FIG. 2A). The chromosome number of the GF-1 cells at subculture 80 was distributed between 17 and 42 in 100 cells examined, and had a bimodal distribution with modes set at 32 and 36 (FIG. 2B). Both micro- and macro-chromosomes were found in metaphase-arrested cells.

Plating Efficiency

The plating efficiency of the GF-1 cells seeded at a density of 100 cells/flask was 21% at subculture 50 which increased to 80% at subculture 80. In comparison, the plating efficiencies of CF, BPS-1, TO-2 and EK cell lines seeded at a density of 100 cells/flask were 22%, 13%, 48%, and 63%, respectively. The increase in plating efficiency in GF-1 cells suggests the occurrence of transformation during subcultures 50–80.

Effects of FBS Concentration and Temperature on the Growth of the GF-1 Cells

Figure 3A:
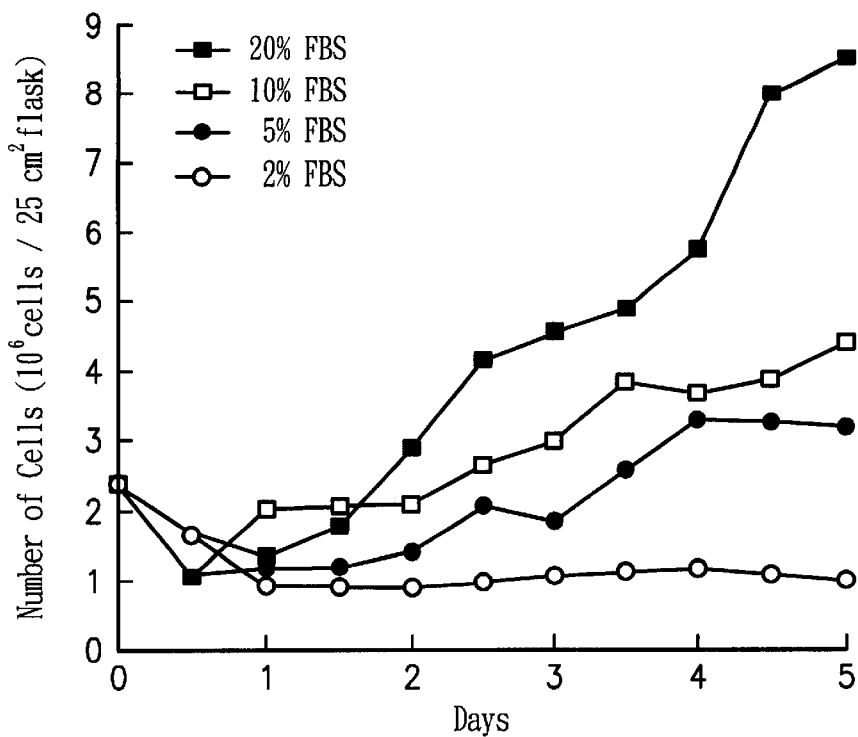
Figure 3B:
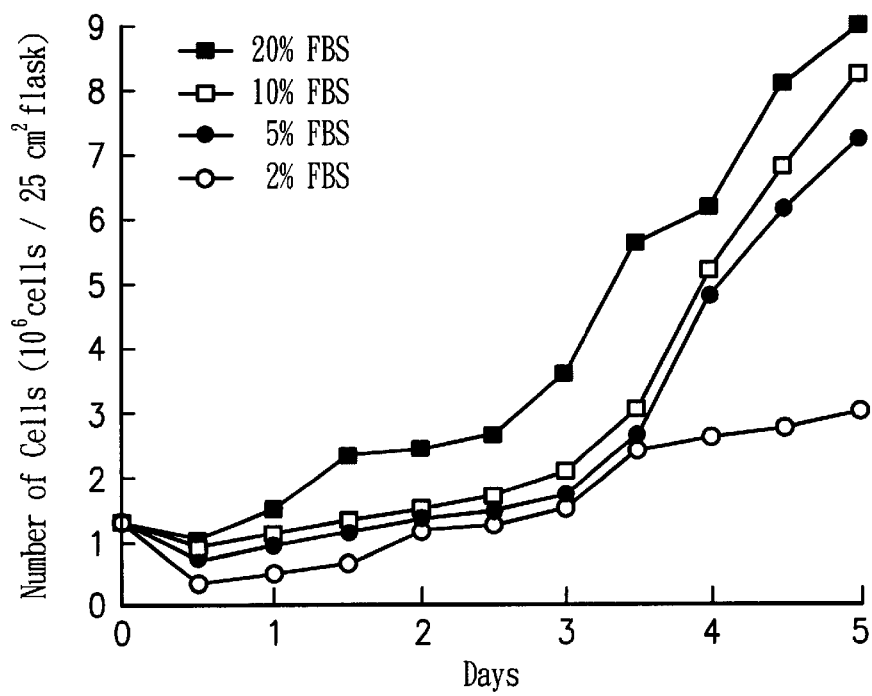

FIG. 3 illustrates the effects of FBS concentration on the growth of the GF-1 cells at subcultures 50 and 80. The growth of the GF-1 cells at both subcultures 50 and 80 corresponded to the concentration of FBS, i.e., the higher the FBS concentration, the greater the growth of cells. However, when the growth rates of the GF-1 cells at subcultures 50 and 80 were compared, the GF-1 cells at subculture 80 demonstrated a much greater growth potential than those at subculture 50, especially when the FBS concentrations were at 2%, 5%, and 10%. For example, at day 4 of the cell cultures containing 10% of FBS, the GF-1 cells at subculture 50 have $3.5 \times 10^6$ cells/25 cm$^2$ flask, whereas the GF-1 cells at subculture 80 have $5.0 \times 10^6$ cells/25 cm$^2$ flask. These results suggest that the requirement of FBS for cell growth decreased at subculture 80, which is an indication that the transformation of cells had occurred during the period from subculture 50 to subculture 80.

Figure 4:
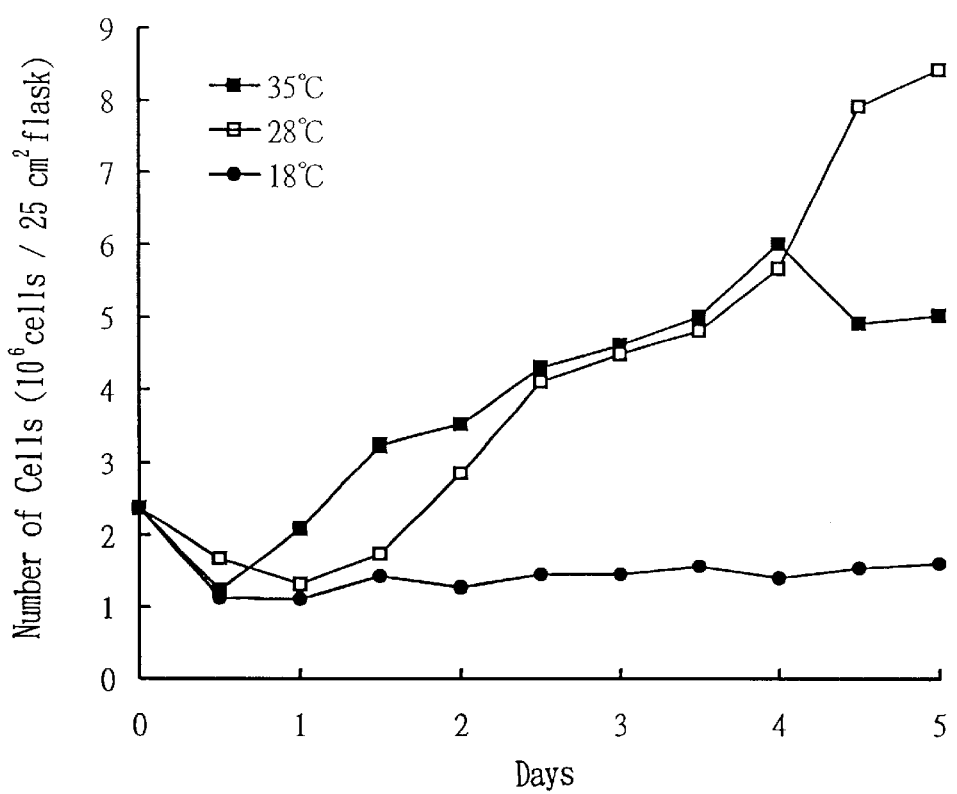
Figure 5A:
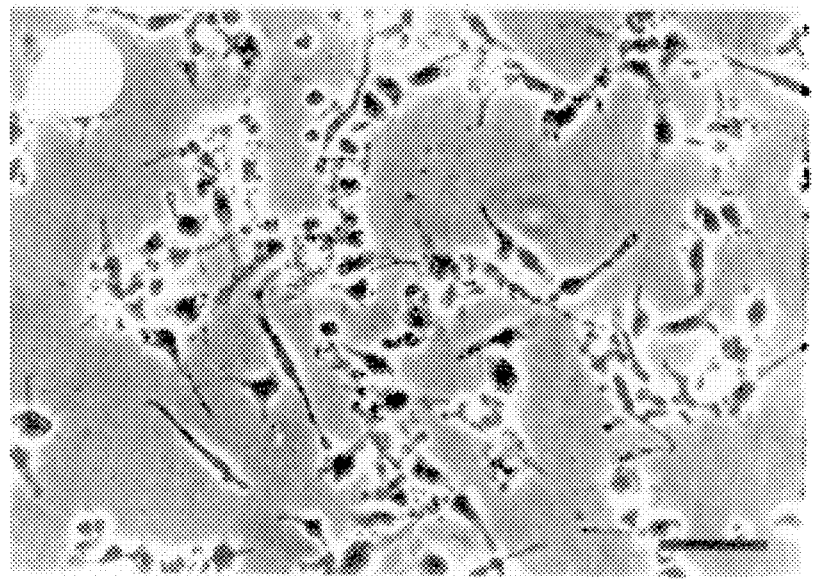
Figure 5B:
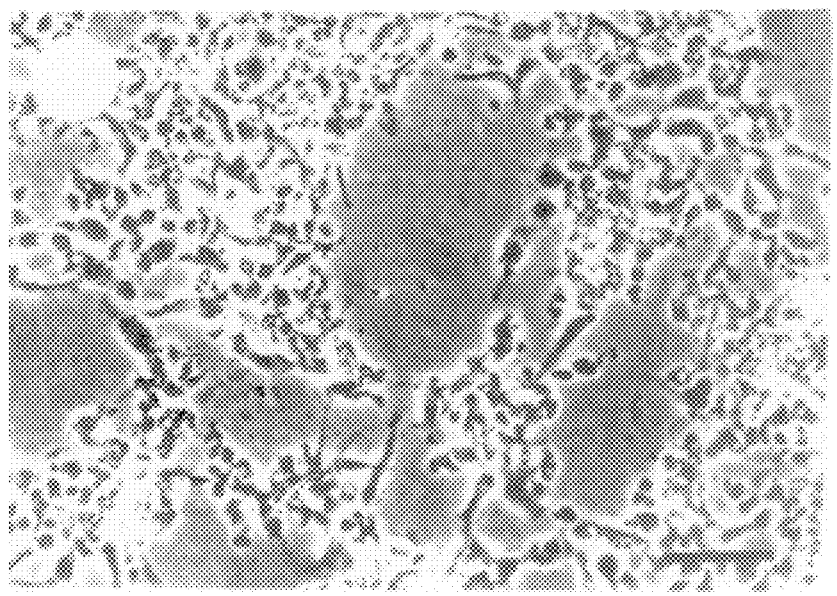
Figure 5C:
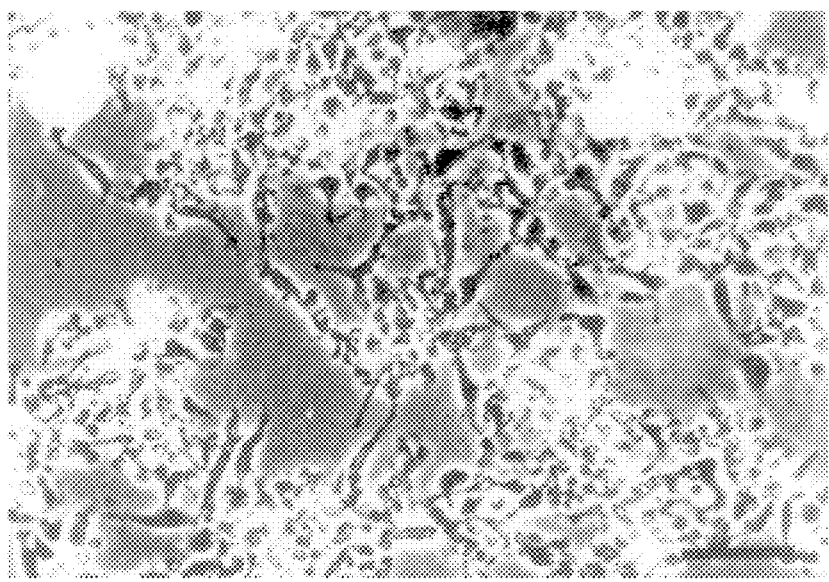
Figure 5D:
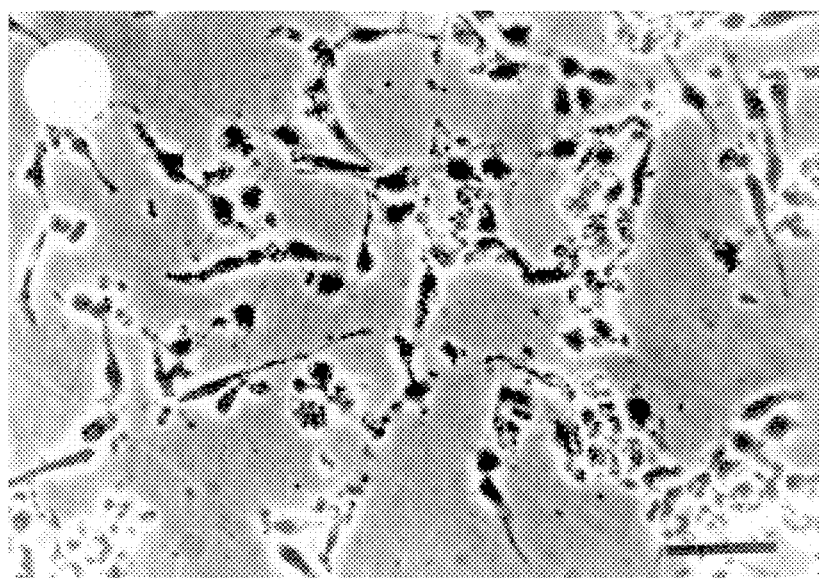
Figure 5E:
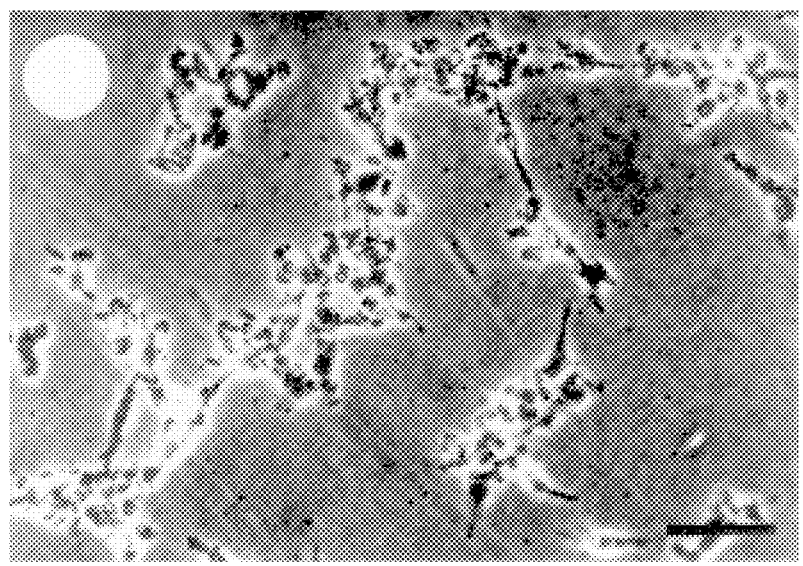
Figure 5F:
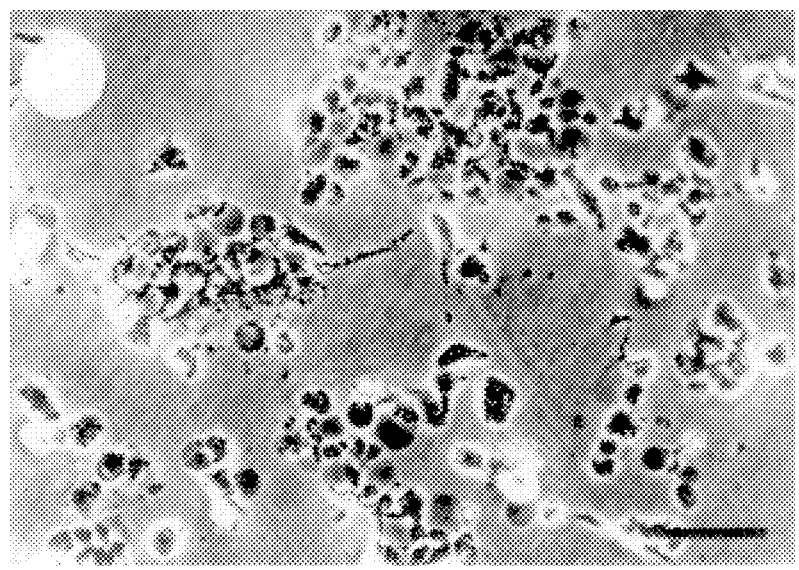
Figure 5G:
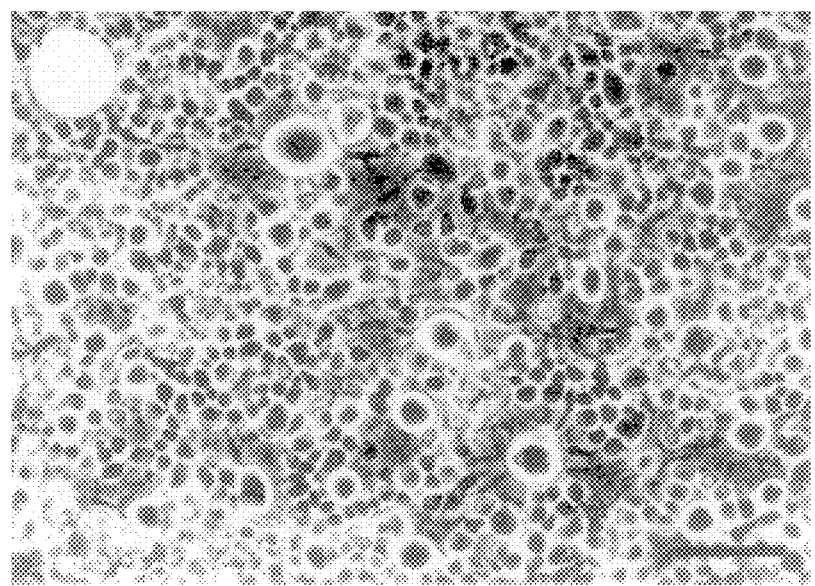
Figure 5H:
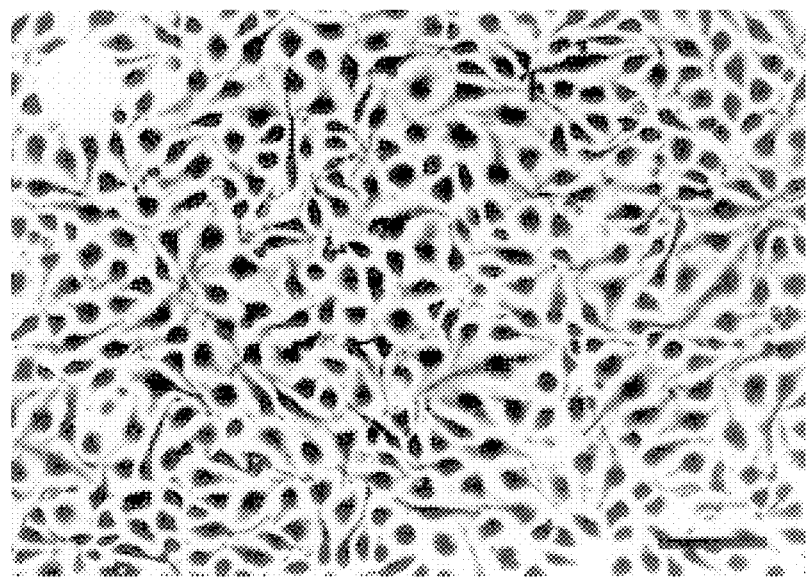

FIG. 4 illustrates the effect of temperature on the growth of the GF-1 cells at subculture 80. The results show that the GF-1 cells grew well at 28° C. and 35° C. However, the growth of the GF-1 cells cultured at 35° C. started to decline at day 4, suggesting that maintaining the cell culture at 35° C. may have long-term effects on cell growth. The GF-1 cells did not grow well at 18° C.

In accordance with a second embodiment of the present invention, there are provided methods for producing the aquatic viruses in the GF-1 cells, purifying the viruses, and detecting a virus in the immortal cell line. The experimental designs pertaining to this embodiment are illustrated as follows:

EXAMPLE 2

METHODS FOR PRODUCING VIRUSES USING THE GF-1 CELL LINE AND METHODS FOR DETECTING THE VIRUSES IN THE CELL LINE (1) Test for Susceptibility of the GF-1 Cells to Aquatic Viruses Infectious pancreatic necrosis virus (IPNV, strain AB, SP, VR299 and EVE), hard clam reovirus (HCRV), eel herpes virus Formosa (EHVF) and nervous necrosis virus (NNV, GNNV isolate) were used to infect the GF-1 cells at subculture 80. The susceptibility to GNNV was also examined in BGF-1 cell line, which was derived from the fin of the banded grouper *Epinephelus awoara*.

Each of the monolayer GF-1 cells was inoculated with 0.5 ml of various aquatic virus with titer of $10^3$TCID$_{50}$/0.1 ml. After a 30-min adsorption period, the cells from each flask were washed three times with PBS, followed by the addition of 5 ml of L15-2% FBS to each flask. The flasks were then incubated separately at 20° C. and 28° C. The supernatants of culture cells were collected and titrated for 6 days post viral infection.

(2) Multiplication and Purification of Aquatic Viruses in the GF-1 Cell Line

Viral isolate was inoculated at an MOI (multiplicity of infection) of 0.01 into the GF-1 cell line. When CPE appeared, the GF-1 cells were scraped into the medium and the cell debris was pelleted at 10000×g for 30 min (the first pellet). The supernatant was transferred to a bottle and polyethylene glycol (PEG, molecular weight 20000) and NaCl were added to reach a final concentration of 5% and 2.2% separately. The supernatant was then stirred for 4–6 hours at 4° C., and the virus particles were pelleted by centrifugation at 10000×g for 1 hour (the second pellet). The first pellet and the second pellet were re-suspended in a small amount of TNE buffer (0.1M Tris, 0.1M NaCl, 1 mM EDTA, pH 7.3), to which an equal volume of Freon 113 was added. The mixture was shaken vigorously for 5 min, and the emulsion was separated into the Freon and aqueous phase by centrifugation at 3000×g 10 min. The aqueous phase was collected, layered on a preformed 10–40% (w/w) CsCl gradient, and centrifuged at 160000×g for 20 hours. The visible virus band was collected, diluted with 10 ml of TNE buffer, and pelleted again by centrifugation at 150,000 g for 1 hours. The final pellet was resuspended in a small volume of TE buffer (0.1 M Tris, 1 mM EDTA, pH 7.3).

(3) Detection of Aquatic Viruses in the GF-1 Cell Line

In general, when a virus infects a cell line which is susceptible to the virus, a CPE of the cell culture can be observed within a couple of days after the infection. The appearance of CPE serves as evidence that the virus has successfully infected and multiplied in the cell line. The viral infection in the cell line can be further confirmed using an electron microscopic technique which is described as follows: The virus-infected cells were fixed in 2.5% glutaraldehyde in 0.1M of phosphate buffer at pH 7.4 and post-fixed in 1% of osmium tetraoxide. The cells were ultrathin sectioned. The ultrathin sections were stained with uranyl acetate-lead citrate and examined under a Hitachi H-600A electron microscope. The viral particles should appear as homogeneous, spherical particles in the cytoplasm of the cells.

There are also three methods which are directed to specific detection of NNV in the GF-1 cell line:

(A) Detection of NNV in the GF-1 Cells by Polymerase Chain Reaction (PCR) Amplification A PCR amplification method was used to confirm that the GF-1 cells are able to proliferate NNV. The method required that the viral RNA be extracted from the supernatant of the NNV-infected cells after CPE appeared using a Rneasy™ mini kit (QIAGEN). For reverse transcription, extracted viral RNA was incubated at 42° C. for 30 min in 40 □l of 2.5×PCR buffer (25 mM of Tris-HCl, pH 8.8, 3.75 mM of MgCl$_2$, 125 mM of KCl, and 0.25% of Triton X-100) containing 2 U of MMLV reverse transcriptase (Promega), 0.4 U of RNsin (Promega), 0.25 mM of dNTP, and 0.5 □M of the reverse primer R3 (5' CGAGTCAACACGGGT-GAAGA 3') (SEQ ID NO. 1). Following the cDNA synthesis, 40 □l of the cDNA mixture were diluted 2.5-fold with diethyl pyrocarbonate (DEPC)-treated H$_2$O (containing 0.025 U of DNA polymerase [Biometra], 0.1 mM of dNTP and 0.5 □M of the forward primer F2 [5' CGTGTCAGT-CATGTGTCGCT 3'] [SEQ ID NO.2]), and incubated in an automatic thermal cycler (TouchDown™ thermal cycler, Hybaid company). The target region for the primer set (F2, R3) is T4 (400 bp). The PCR products corresponding to T2 and T4 were amplified from the nucleic acids of NNV-infected GF-1 cells.

(B) Detection of NNV in the GF-1 Cells by Western Immunoblot

A western immunoblot method was used to specifically detect the NNV proteins. The viral sample was prepared as follows: NNV was inoculated into the GF-1 cells and incubated at 20–32° C. After 5 days of incubation, the NNV-infected cells were pelleted by centrifugation at 1000 g for 10 min. The cell pellets were loaded onto a 10% SDS-polyacrylamide gel. After electrophoresis, the proteins were blotted to an immobilon-P transfer membrane (Millipore), which was then soaked in a 3% skim milk tris buffered saline (TBS) for 1 hr. The membrane was then incubated with an antiserum against NNV for 1 hr at room temperature, washed with TBS, reacted with a peroxidase-conjugate goat system for 1 hr, and stained with a substrate containing 6 mg of 4-chloronaphthol in 20 ml of methanol and 60 □l of H$_2$O$_2$ in 100 ml of TBS.

(C) Detection of NNV in the GF-1 Cells by Enzyme-Linked Immunoabsorbent Assay (ELISA)

ELISA is an immunological method which uses an enzyme-labeled immunoreactant (antigen or antibody) and an immunosorbent (antigen or antibody bound to a solid) to identify specific serum or tissue antibodies or antigens. The ELISA test was conducted as follows: an effective amount of purified NNV proteins was coated onto a microtiter plate at 4° C. overnight. Then, 3% of bovine serum albumin (BSA) was added to the plate (used as blocking agent) and incubated at 37° C. for 1 hr. The plate was then washed 3 times with buffer. Next, a diluted rabbit anti-NNV serum was added to the plate and incubated at 37° C. for 1 hr. This was followed by the addition of goat anti-rabbit IgG-horseradish peroxidase serum at 37° C. for 1 hr and 3,3',5,5'-tetramethyl benzidine was added for color development. The color reaction was stopped with 1 N H$_2$SO$_4$. The optical density of the wells in the microtiter plate was measured at 450 nm with an ELISA reader (Dynatech MR 5000).

(D) Detection of NNV in the GF-1 Cells by Immunofluorescent Staining

To detect the virus that proliferated in the GF-1 cells, cell cultures were fixed by 10% formalin for 12 hrs after viral infection. The fixed cell cultures were treated with 0.2% of Triton X-100 and washed with PBST (phosphate buffer with 0.05% Tween 20). The Triton-treated cell cultures were further washed with 3% of skim milk as blocking agent and then reacted with mouse anti-NNV serum. Finally, the antibody-treated cell cultures were stained with fluorescein isothiocyanate (FITC) conjugated goat anti-mouse antibodies.

Results

Table 1 summarizes the results of virus susceptibilities of the GF-1 cells to IPNV (AB, SP, VR299, EVE strains), HCRV, EHVF and NNV (GNNV isolate), which were determined by first observing the appearance of CPE in the cells after the viral inoculation, followed by the determination of viral titers (TCID$_{50}$/ml)

TABLE 1

Viral Susceptibilities of GF-1 Cells at Subculture 80

| Cell line | Virus | Initial Viral Inoculum (TCID$_{50}$) | CPE 28° C. | CPE 20° C. | Virus Yield/ml (TCID$_{50}$/ml) 28° C. | Virus Yield/ml (TCID$_{50}$/ml) 20° C. |
|---|---|---|---|---|---|---|
| GF | IPNV | | | | | |
| | AB | $10^3$ | − | + | ND | $10^{9.5}$ |
| | SP | $10^3$ | − | + | ND | $10^{10.8}$ |
| | VR299 | $10^3$ | − | + | ND | $10^{9.8}$ |
| | EVE | $10^3$ | − | + | ND | $10^{9.6}$ |
| | HCRV | $10^3$ | − | + | ND | $10^{11.0}$ |
| | EHVF | $10^3$ | + | + | $10^{8.1}$ | $10^{7.0}$ |
| | GNNV | $10^3$ | + | − | $10^{8.3}$ | ND |

ND: Not done. +: Cytopathic effect (CPE) was observed.

As shown in Table 1, for the IPNV strains and HCRV, CPE appear only when the cells are incubated at 20° C. For EHVF, CPE appears at both 20° C. and 28° C. However, for GNNV, CPE appears at 28° C. The yields of the viruses in GF-1 cells at subculture 80, which are ranged between $10^{7.0}$ (as for EHVF at 20° C.) and $10^{11.0}$ (as for HCRV at 20° C.), are extremely high.

Typically, for an aquatic virus such as GNNV, CPE began at the 3rd day of infection when some rounded, granular, retractile cells began to appear in the cell culture (FIG. 5). Soon more and more cells became round and swollen. The swollen cells became larger and finally started to detach from the cell culture and float in the culture media. Most of the detached cells were completely disintegrated. The culture fluid from cell culture showing CPE could transmit other GF-1 cells. This experiment also tested the susceptibility of BGF-1 cell line (derived from the fin of the banded grouper Epinephelus awoara) to GNNV. The results showed that no CPE was found after the viral infection.

Figure 7:
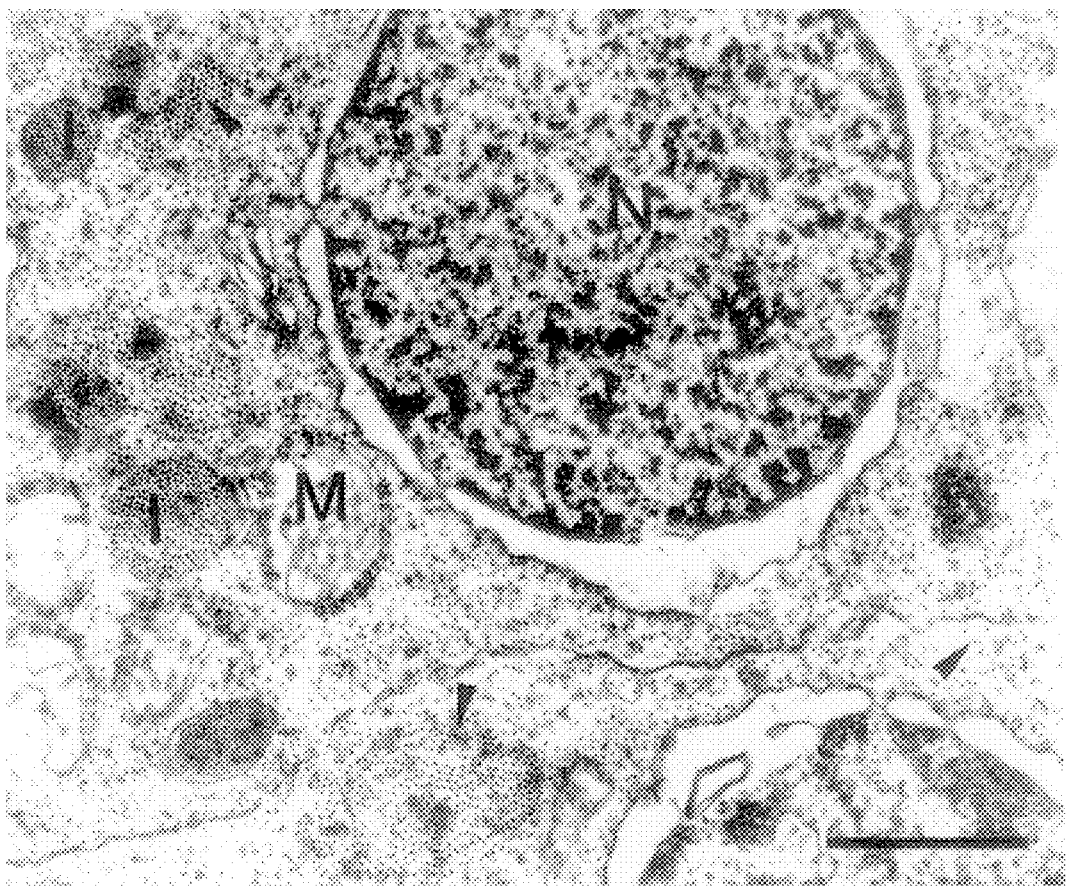

Typically, for an aquatic virus such as GNNV, the virus could be observed in the cytoplasm of the GF-1 cells under electron microscope as numerous non-enveloped, homogeneous, spherical to icosahedral particles with diameter of 20–25 nm (FIG. 7). Some of the viral particles were included in the inclusion bodies and the others could be found in the cytoplasm (FIG. 7). The isolated viral particles could be further purified by CsCl density gradient centrifugation. Using GNNV as an example, the purified virus was a non-enveloped icosahedral virion particle with the diameter of 20–25 nm. The buoyant density of GNNV in CsCl was 1.34 g/cm$^3$.

In addition to the findings of CPE in the GF-1 cells, the existence of an aquatic virus in the GF-1 cells and the capability of the cells to multiply the virus can be further confirmed by four methods: (1) the PCR method; (2) the Western immunoblot method; (3) the ELISA method; and (4) the immunofluorescent staining method.

Figure 6:
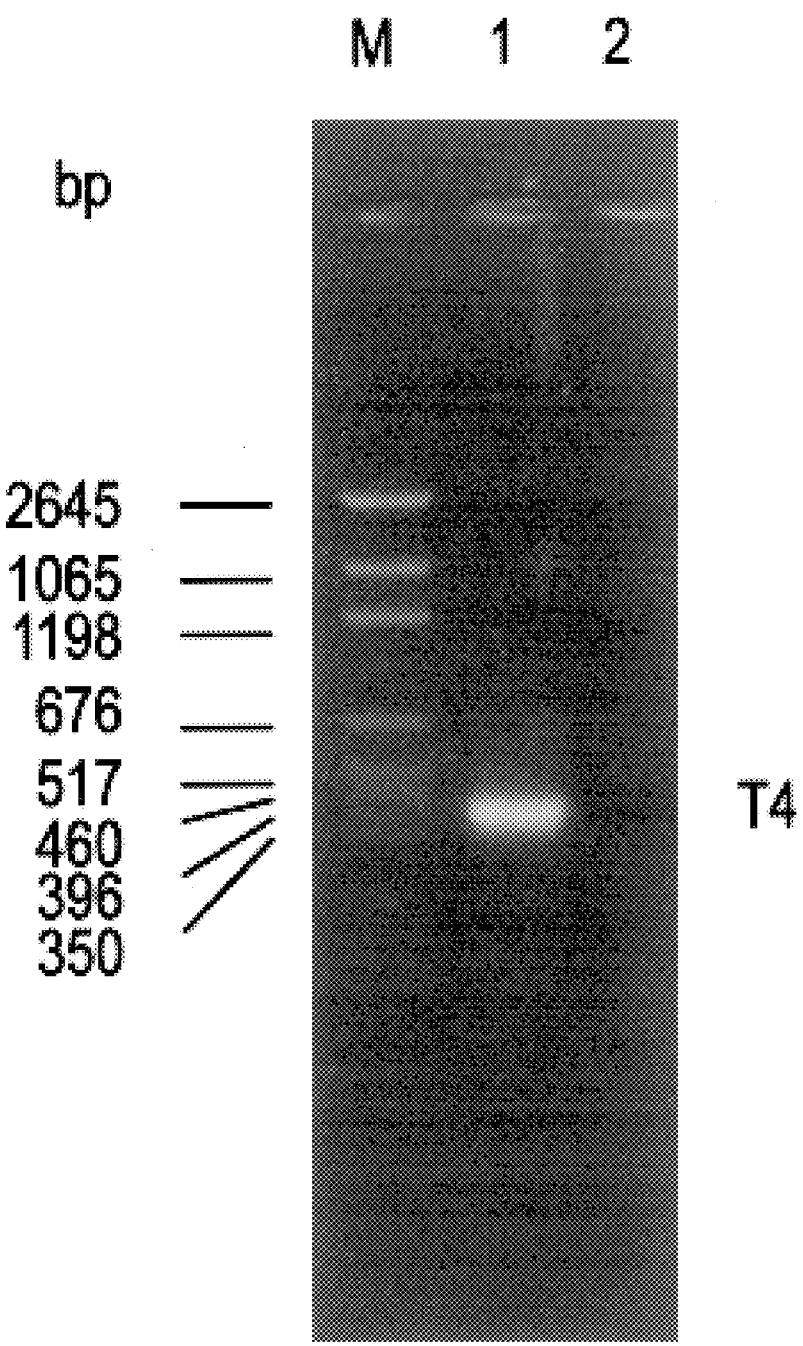

Using GNNV as an example, the PCR method could be accomplished by choosing a pair of primers, i.e., R3 (SEQ ID NO.1) and F2 (SEQ ID NO.2), for PCR amplification. The target fragment T4 exists in fish nodavirus. Therefore, the PCR method using F2 and R3 was specific to fish nodavirus, not just GNNV. The results of the PCR study showed that GNNV could be replicated in the GF-1 cells and released into the supernatant of culture cells (FIG. 6).

The Western immunoblot using mouse anti-GNNV serum demonstrated that viral proteins were present in the GNNV-infected cells cultured at 20–32° C., suggesting that the viral mRNA could be successfully translated into viral polypeptides within the host cells when the culture was maintained at 20–32° C.

The ELISA and immunofluorescent staining methods also showed positive reactions with the anti-GNNV serum, indicating that GNNV could be multiplied in the GF-1 cells.

In accordance with a third embodiment of the present invention, there is provided for an anti-NNV antibody and the method of making the antibody. The experimental designs in this embodiment are illustrated as follows:

EXAMPLE 3

PRODUCTION OF ANTI-NNV ANTIBODIES (1) Production of Anti-NNV Antibodies

Polyclonal antibodies can be produced in accordance with conventional methods, e.g., by sequential injections of the purified NNV immunogen into a suitable animal such as a rabbit, rat, or mouse. For example, a suitable amount of the NNV immunogen can be injected intravenously, subcutaneously, or intraperitoneally to a rabbit and boosted twice or more at 2 or 3 week intervals. The injection may contain a suitable amount of Freund's complete or incomplete adjuvant, if necessary.

For the production of monoclonal antibodies, immunizing mice is preferred. Three or four days after the final boost, spleen cells of mice can be separated and fused with myeloma cells, e.g., SP2/0-Ag14 myeloma cells (ATCC CRL 1581), in accordance with a conventional method described by Mishell and Shiigi (Selected Methods in Cellular Immunology, W.H. Freeman & Company, 1980). The spleen cells and the myeloma cells can be used in a ratio ranging from 1:1 to 1:4. A fusion-promoting agent, e.g., polyethylene glycol (PEG) 4000, may be employed for accelerating the cell fusion. A medium suitable for use in the cell fusion step may be RPMI 1640 (Gibco BRL, Life Technologies, Inc.) and the medium generally contains 10–15% (v/v) fetal bovine serum (FBS).

The fused cells can be cultured in the RPMI1640-15% FBS, supplemented with hypoxanthine, thymidine and aminopterin, and after seven to ten days, positive hybridoma clones producing antibodies specific for NNV can be selected by ELISA assay using the culture supernatant. Further selection of positive clones can be accomplished by using conventional methods, e.g., the limiting dilution technique, the plaque method, spot method, agglutination assay and autoradiographic immunoassay.

(2) Purification of Antibodies

Antibody can be purified by conventional immunoglobulin purification procedures such as ammonium sulfate precipitation, gel electrophoresis, dialysis, affinity chromatography, and ultrafiltration. Ion exchange, size exclusion hydroxylapatite, or hydrophobic interaction chromatography can be employed, either alone or in combination. Light and heavy chain can be carried out using gel electrophoretic techniques or isoelectric focusing, as well as other techniques known in the art.

In accordance with a fourth embodiment of the present invention, there is provided a vaccine to NNV and a method for protecting fish against NNV infection. The experimental designs in this embodiment are illustrated as follows:

EXAMPLE 4

PRODUCTION OF NNV VACCINES

Preparation of Vaccine Using Killed NNV

The vaccine of the present invention is administered as a killed vaccine, which encompasses any methods now known or hereafter developed for killing. The preferable method is by heat treatment. The heat treatment method can be accomplished by heating the purified NNV to a temperature sufficiently to inactivate the virus (such as 70° C.) for a sufficient amount of time (such as for 24 hours). After the heating step has been completed, for intraperitoneal or intramuscular vaccination, the inactivated NNV can be emulsified in Freund's incomplete adjuvant (FIA) using a mixer for several minutes. The vaccine can then be injected into the fish (the primary injection). Booster injections can be given to the fish 30–45 days after the primary injection. Normally, the booster injection consists of about one half of the volume of the vaccine used in the primary injection. The fish then can receive a secondary boost 10 days after the first booster shot is administered. The serum samples from the fish at various time points can be taken for titer determination.

For orally administered vaccine, an enteric coating containing non-toxic polymeric materials can be added to the vaccine. The preferable enteric coating materials are the ones which can resist dissolution at the pH of the stomach but can be dissolved once the material passes from the stomach to the pyloric caecum and intestines. For example, cellulose acetate phthalate, hydroxypropylmethyl cellulose phthalate, carboxymethylethyl cellulose, hydroxypropylmethyl cellulose acetate succinate, cellulose acetate trimellitate, polyvinyl acetate phthalate, EUDAGRIT L-30D and 1100-55, EUDAGRIT L 12.5, and L 100, EUDRAGIT E, RL, RS and NE are among the preferred materials. Additional materials can be used in combination with the enteric coating materials. For instance, plasticizers (such as polyethylene glycol 200, 400, 1000, 4000, 6000, propylene glycol, PVPK-90, glycerin or glycerol, diethyl phthalate, oleic acid, isopropyl myristate, liquid paraffin or mineral oil, triacetin, glycerol monostearate, dibutyl sebacate, triethyl citrate, tributyl citrate, acetylated monoglyceride, dibutyl phthalate, acetyl tributyl citrate, castor oil, and glycerol tributyrate); disintegrants (such as sodium starch glycolate); adjuvants (such as immunostimulants [e.g., beta glucan]); binders (such as starch, polyvinyl pyrrolidone, polyvinyl alcohol); diluents (such as lactose); lubricants (such as magnesium stearate) etc. can all be used with the enteric coatings. For oral administration, fish can receive the vaccine on an every-other-day basis for a total of thirty days. The effects of the vaccines can be monitored by the use of ELISA.

Orally administered vaccine is generally the preferred method of vaccinating fish because it is not limited by the size of the fish that can be handled, and it reduces the stress on the fish associated with immersion and intraperitoneal injection. Furthermore, oral vaccines offer the additional advantages of stimulating the gut-associated lymphoid tissue to a greater extent than does intraperitoneal injection.

The present invention has been described with reference to several preferred embodiments. Other embodiments of the invention will be apparent to those skilled in the art from the consideration of this specification or practice of the invention disclosed herein. It is intended that the specification and examples contained herein be considered as exemplary only, with the true scope and spirit of the invention being indicated by the following claims:

What is claimed is:

1. An immortal cell line which is ATCC deposit no. PTA-859.

2. The immortal cell line of claim 1, wherein said cell line is derived from grouper fin tissue.

3. The immortal cell line according to claim 2, wherein said cell line is susceptible to and mass produces a virus.

4. The immortal cell line according to claim 3, wherein said virus is selected from the group consisting of Birnaviridae, Herpesviridae, Reoviridae, and Nodaviridae.

5. The immortal cell line according to claim 4, wherein said Birnaviridae is Infectious Pancreatic Necrosis Virus (IPNV).

6. The immortal cell line according to claim 4, wherein said Herpesviridae is Eel Herpes Virus Formosa (EHVF).

7. The immortal cell line according to claim 4, wherein said Reoviridae is Hard Clam Reovirus (HCRV).

8. The immortal cell line according to claim 4, wherein said Nodaviridae is a fish nodavirus which is selected from the group consisting of Nervous Necrosis Virus (NNV), Fish Encephalitis Virus (EFV), Piscine Neuropathy Nodavirus (PNN), Grouper Nervous_Necrosis Virus (GNNV), Stripped Jack Nervous Necrosis Virus (SJNNV), Tiger Puffer Nervous Necrosis Virus (TPNNV), Berfin Flounder Nervous Necrosis Virus (BFNNV) and Red Spotted Grouper Nervous Necrosis Virus (RGNNV).

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<221> NAME/KEY: primer_bind
<222> LOCATION:
<223> OTHER INFORMATION: synthetic oligonucleotide primer
    complementary to viral sequence
<300> PUBLICATION INFORMATION:

<400> SEQUENCE: 1
cgagtcaaca cgggtgaaga                    20

<210> SEQ ID NO 2
<211> LENGTH: 20
<212> TYPE: DNA
<213> ORGANISM: Artificial Sequence
<220> FEATURE:
<221> NAME/KEY: primer_bind
<222> LOCATION:
<223> OTHER INFORMATION: synthetic oligonucleotide primer
    complementary to viral sequence
<300> PUBLICATION INFORMATION:

<400> SEQUENCE: 2
cgtgtcagtc atgtgtcgct                    20